(12) United States Patent
Ichikawa et al.

(10) Patent No.: US 8,952,203 B2
(45) Date of Patent: Feb. 10, 2015

(54) METHOD FOR MANUFACTURING HYDROXYL GROUP-CONTAINING ACETAL COMPOUND

(75) Inventors: Takashi Ichikawa, Kanagawa (JP); Shuichi Yoshimura, Kanagawa (JP); Ken-ichiro Nakamoto, Kanagawa (JP)

(73) Assignee: NOF Corporation, Tokyo (JP)

( * ) Notice: Subject to any disclaimer, the term of this patent is extended or adjusted under 35 U.S.C. 154(b) by 406 days.

(21) Appl. No.: 13/428,671

(22) Filed: Mar. 23, 2012

(65) Prior Publication Data

US 2012/0277477 A1    Nov. 1, 2012

(30) Foreign Application Priority Data

Mar. 25, 2011 (JP) ................. 2011-067148

(51) Int. Cl.
  *C07C 41/58* (2006.01)
  *C07C 43/315* (2006.01)
(52) U.S. Cl.
  CPC ............... *C07C 41/58* (2013.01); *C07C 43/315* (2013.01)
  USPC ........................................................ 568/600
(58) Field of Classification Search
  CPC .............................. C07C 41/58; C07C 43/315
  USPC ........................................................ 568/600
  See application file for complete search history.

(56) References Cited

U.S. PATENT DOCUMENTS

| 5,925,720 A | 7/1999 | Kataoka et al. |
| 6,590,043 B1 | 7/2003 | Nagasaki et al. |
| 6,974,856 B1 | 12/2005 | Kataoka et al. |
| 2005/0176896 A1 | 8/2005 | Bentley et al. |

FOREIGN PATENT DOCUMENTS

| CN | 1187829 A | 7/1998 |
| JP | 04-346959 A | 12/1992 |
| JP | 09-302048 A | 11/1997 |
| JP | 11-322916 A | 11/1999 |
| JP | 2001-48978 A | 2/2001 |
| JP | 3310303 B2 | 8/2002 |
| JP | 2003-113214 A | 4/2003 |
| JP | 3855279 B2 | 12/2006 |
| WO | 97/42242 A1 | 11/1997 |
| WO | 98/46655 A1 | 10/1998 |
| WO | 01/10934 A1 | 2/2001 |

OTHER PUBLICATIONS

Jan Erik Vik, "Studies in Intermediates Involved in the Syntheses of Pentaerythritol and Related Alcohols. II.*Syntheses of x-Hydroxymethyl-substituted Aldehydes", Acta Chemica Scandinavica 27, 1973, No. 1, pp. 239-250.

Akiyama, et al., "Synthesis of Poly(ethylene glycol)-block-poly(ethylenimine) Possessing an Acetal Group at the PEG End", Macromolecules, 2000, vol. 33, No. 16, pp. 5841-5845.

International Search Report and Written Opinion, dated Jun. 12, 2012, issued by the International Searching Authority in counterpart International Application No. PCT/JP2012/057457 (PCT/ISA/210).

Office Action, dated Jul. 2, 2014, issued by the State Intellectual Property Office of the People's Republic of China in counterpart Chinese Application No. 201280015250.1.

*Primary Examiner* — Rosalynd Keys
(74) *Attorney, Agent, or Firm* — Sughrue Mion, PLLC

(57) ABSTRACT

A method for manufacturing an acetal compound represented by the formula [1] in which the steps (A) to (D) as defined herein are performed sequentially, and an acetal compound of the formula [1] which is produced by the method:

[1]

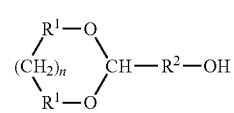

wherein n is 0 or 1 provided that $R^1$ groups may be bonded or may not be bonded to each other when n is 0; $R^1$ is an alkyl group having 1 or 2 carbon atoms or an alkylene group having 1 or 2 carbon atoms and the $R^1$ groups may be same or different from each other; and $R^2$ is an alkylene group having 1 or 6 carbon atoms.

16 Claims, No Drawings

METHOD FOR MANUFACTURING HYDROXYL GROUP-CONTAINING ACETAL COMPOUND

FIELD OF THE INVENTION

The present invention relates to a method for manufacturing an acetal compound having a hydroxyl group in the molecule.

BACKGROUND OF THE INVENTION

Recently, as a drug delivery material for improving circulation in blood of pharmaceuticals and physiologically active substances and imparting a targeting function toward a target site, a polyalkylene glycol derivative has been utilized. Since more improved circulation in blood is observed as the molecular weight of a polyalkylene glycol increases, a polyalkylene glycol derivative having a molecular weight of thousands or more has been frequently used. Moreover, as a functional group to be utilized for binding to drugs, an aldehyde group has excellent characteristic features that it forms a Schiff base with a primary amine and forms a more stable secondary amine through reductive amination and also the shift of isoelectric point is small since the secondary amine is present even after the binding. Furthermore, in the case where a pharmaceutical to be a target is a protein, since an aldehyde group can be bound to an N-terminal amine group depending on reaction conditions, an aldehyde group is also excellent in view of selectivity of binding site. Therefore, a polyalkylene glycol derivative having an aldehyde group has been widely used for binding to pharmaceuticals having an amino group. As a commercially available example of pharmaceutical modification of the polyalkylene glycol derivative having an aldehyde group, there is mentioned a pharmaceutical in which granulocyte colony-stimulating factor (G-CSF) is modified with a polyalkylene glycol derivative having a molecular weight of 20,000, and the pharmaceutical has gained a large sales. Currently, development of generic drugs, application to the other pharmaceuticals, and the like have been actively investigated and thus there is an increasing demand for the polyalkylene glycol derivative having an aldehyde group.

As methods for synthesizing the polyalkylene glycol derivative having an aldehyde group, there are following two manufacturing methods. In the first method, after the hydroxyl group of an acetal compound having a hydroxyl group is converted into an alcoholate or the like to enhance reactivity and then bound to a polyalkylene glycol terminal, the acetal group is hydrolyzed to synthesize a terminal aldehyde compound. In the second method, after an alkylene oxide is addition-polymerized to the hydroxyl group of an acetal compound having a hydroxyl group under an alkali catalyst, the acetal group is hydrolyzed. In both methods, as a raw material for the polyalkylene glycol derivative having an aldehyde group, there is employed a compound having an acetal group that is a protective group of aldehyde and a hydroxyl group in the molecule.

When a reactive impurity having a hydroxyl group is present in the acetal compound raw material, the impurity is converted into a polyalkylene glycol derivative other than the objective compound in each method, through binding of the impurity to the polyalkylene glycol derivative in the former method or through addition polymerization of the alkylene oxide in the latter method. When such an impurity remains, purity of the pharmaceuticals decreases and also it may be a main cause of inducing heterogeneity and performance inhibition, resulting in a serious problem.

As a difference between the impurity having a polyalkylene glycol structure formed as a by-product and the polyalkylene glycol derivative having an aldehyde group as an objective compound, a terminal structure is slightly different from each other within the molecular weight of several thousands to several tens of thousands. Therefore, chemical properties are similar and thus it is very difficult to purify the polyalkylene glycol derivative. In a high molecular weight range where the circulation in blood is improved, the property difference from the objective compound further decreases, so that purification becomes difficult. Moreover, since such a reactive substituent as an aldehyde group is present, there is rather a possibility that a side reaction may be induced to lower the purity depending on a purification operation. For the above reasons, in order to manufacture a highly pure polyalkylene glycol derivative, it is necessary to manufacture the acetal compound, which is a raw material for the polyalkylene glycol derivative, in high purity.

As the reactive impurity in the acetal compound having a hydroxyl group as a raw material, a polyacetal, an alcohol, and an antioxidant may be mentioned.

With regard to the polyacetal, since an acetal group is generally prone to undergo decomposition by heat, the polyacetal is formed as a by-product through intermolecular acetal exchange. The alcohol is formed as a by-product through elimination of the alcohol that has formed the acetal group at the above polyacetalization. With regard to the antioxidant, the following contamination mechanism may be present other than the addition thereof for the purpose of improving stability of the objective compound. For example, in Non-Patent Document 1 (ACTA CHEMICA SCANDINAVIA 27 (1973) 239-250), an acetal compound having an ethyl ester is reduced with lithium aluminum hydride to synthesize the acetal compound having a hydroxyl group. In the reduction reaction, an ether solvent is generally employed. Usually, an aliphatic ether such as diethyl ether or tetrahydrofuran to be used as the ether solvent is added with an antioxidant such as 2,6-di-tert-butyl-p-cresol (BHT) for the purpose of preventing the solvent from being oxidized with oxygen to form a peroxide. Thus, when the ether solvent is used for the synthesis, BHT is entrained.

These three kinds of impurities are entrained in the methods for manufacturing the acetal compound having a hydroxyl group, which have hitherto been reported. For example, as an example where the acetal compound having a hydroxyl group is bound to a polyalkylene glycol derivative, in Patent Document 1 (US2005/0176896 A1), after 3,3-diethoxy-1-propanal is subjected to azeotropic dehydration in toluene, it is converted into an alcoholate and then bound to the polyalkylene glycol derivative. In this method, impurities having a hydroxyl group, such as a polyacetal and BHT, which have a boiling point higher than that of toluene, remain.

Moreover, as an example where an alkylene oxide is addition-polymerized to an acetal compound having a hydroxyl group, Non-Patent Document 2 (Macromolecules 2000, 33, 5841-5845) may be mentioned. In the Document, 3,3-diethoxy-1-propanol is distilled and there is a problem that BHT that is a subliming substance is sublimed and thus coexists with the objective compound and a polyalkylene glycol derivative having a BHT structure at the terminal is formed as a by-product.

PRIOR ART DOCUMENTS

Non-Patent Documents

Non-Patent Document 1: "ACTA CHEMICA SCANDINAVIA" 27 (1973) 239-250

Non-Patent Document 2: "Macromolecules 2000, 33, 5841-5845"

Patent Document

Patent Document 1: US2005/0176896 A1

SUMMARY OF THE INVENTION

With regard to the manufacture of the acetal compound having a hydroxyl group, contamination with the polyacetal, the alcohol, and the antioxidant cannot be prevented by hitherto reported manufacturing methods. Therefore, in order to synthesize a highly pure polyalkylene glycol derivative having an aldehyde group, a method for manufacturing the acetal compound having a hydroxyl group in high purity has been required.

An object of the invention is to provide a method for manufacturing an acetal compound having a hydroxyl group in the molecule in high purity, which is a raw material for a polyalkylene glycol derivative having an aldehyde group to be used in pharmaceutical uses.

As a result of extensive studies for solving the above problems, the present inventors have found that, when an antioxidant is removed, polyacetalization is induced by heat during a distillation operation and the like and thus an acetal compound having a hydroxyl group is decomposed with forming an alcohol as a by-product.

Namely, when the antioxidant is removed, stability of the acetal compound having a hydroxyl group is remarkably decreased and a polyacetal and an alcohol, which become impurities at the manufacture of a highly pure polyalkylene glycol derivative, are produced in a large amount. As a result of further extensive studies based on the findings, even when the antioxidant is removed, an acetal compound having an extremely low content of the above impurities can be obtained by performing distillation under reduced pressure at 65° C. or lower and thus a highly pure polyalkylene glycol derivative can be manufactured.

Namely, the invention relates to a method for manufacturing an acetal compound represented by the formula [1], the method comprising performing the following steps (A) to (D) sequentially and also relates to an acetal compound obtained by the method.

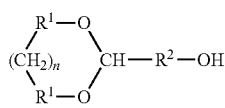

[1]

wherein n is 0 or 1 provided that $R^1$ groups may be bonded or may not be bonded to each other when n is 0; $R^1$ is an alkyl group having 1 or 2 carbon atoms or an alkylene group having 1 or 2 carbon atoms and the $R^1$ groups may be the same or different from each other; and $R^2$ is an alkylene group having 1 to 6 carbon atoms, step (A): a step of dissolving the acetal compound represented by the formula [1] in a solvent made from a hydrocarbon having 5 to 8 carbon atoms in an amount 0.1 mass time or more the amount of the compound of the formula [1] to obtain a solution thereof, step (B): a step of adding a buffer of pH 6 to 10 in an amount 0.5 mass time or more the amount of the compound of the formula [1] to the solution obtained in the step (A) to extract the compound of the formula [1] into the buffer, step (C): a step of adding at least one extracting solvent selected from the group consisting of chloroform and dichloromethane in an amount 0.5 mass time or more the amount of the compound of the formula [1] to the buffer into which the acetal compound has been extracted, thereby extracting the compound of the formula [1] into the extracting solvent to obtain an extraction solution, and step (D): a step of distilling the extraction solution obtained in the step (C) at 65° C. or lower under a reduced pressure of 0.3 kPa or lower.

According to the method of the invention, a hydroxyl group-containing acetal compound having a small content of impurities such as a polyacetal, an alcohol, and an antioxidant can be manufactured. Using the acetal compound obtained by the method of the invention as a raw material, a polyalkylene glycol derivative having an acetal group as a terminal structure, which has an extremely small content of impurities, can be synthesized. Furthermore, since the acetal group can be converted into an aldehyde group through hydrolysis, a highly pure polyalkylene glycol derivative having an aldehyde group can be synthesized. By increasing the purity of the polyalkylene glycol derivative having an aldehyde group, which has been widely used as a drug delivery material, an effect of enhancing performance and homogeneity of pharmaceuticals can be expected.

DETAILED DESCRIPTION OF THE INVENTION

The detail of the invention is a method for manufacturing an acetal compound represented by the formula [1], the method comprising performing the following steps (A) to (D) sequentially.

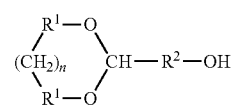

[1]

In the formula [1], n is 0 or 1 provided that $R^1$ groups may be bonded or may not be bonded to each other when n is 0. When n is 0, the formula [1] is represented as the following formula [1a] or [1b]. However, in the case of the formula [1a], $R^1$ is an alkyl group having 1 or 2 carbon atoms. In the case of the formula [1b], $R^1$ is an alkylene group having 1 or 2 carbon atoms.

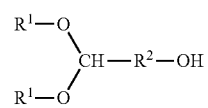

[1a]

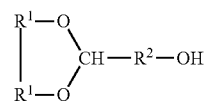

[1b]

Moreover, when n is 1, the formula [1] is represented as follows. In this case, $R^1$ is an alkylene group having 1 or 2 carbon atoms.

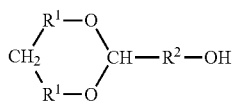
[1c]

R[1] is an alkyl group having 1 or 2 carbon atoms or an alkylene group having 1 or 2 carbon atoms and the R[1] groups may be the same or different from each other.

Specific examples of the acetal group include a dimethoxy group where n is 0 and R[1] is a methyl group, a diethoxy group where n is 0 and R[1] is an ethyl group, a 1,3-dioxolan group where n is 0 and R[1] is a methylene group, a 1,3-dioxane group where n is 1 and R[1] is a methylene group, a 1,3-dioxepane group where n is 0 and R[1] is an ethylene group, a 1,3-dioxocane group where n is 1 and R[1] is a ethylene group, and the like and preferred is the case of a diethoxy group where n is 0 and R[1] is an ethyl group.

R[2] is an alkylene group having 1 to 6 carbon atoms and may be branched in the middle thereof. A preferable embodiment is the case of an ethylene group and, when reactivity in the case of conversion into an aldehyde group is considered, a 1-methylethylene group is also a preferable embodiment.

The following will describe each step in detail. "Step (A): a step of dissolving the acetal compound represented by the formula [1] in a solvent made from a hydrocarbon having 5 to 8 carbon atoms in an amount 0.1 mass time or more the amount of the compound of the formula [1] to obtain a solution thereof"

The step (A) is a step for dissolving the compound of the formula [1] and low polar impurities, mainly an antioxidant such as BHT contained therein.

The hydrocarbon solvent having 5 to 8 carbon atoms includes pentane, hexane, heptane, octane, toluene, and the like and is preferably hexane or heptane, more preferably hexane. When a highly polar solvent is used, since the solvent has a high affinity to the compound of the formula [1] and is difficult to recover into an aqueous layer at a later step, the above solvents are preferred.

The amount of the hydrocarbon solvent is 0.1 mass time or more the amount of the compound of the formula [1] and is preferably 0.1 to 10 mass times, more preferably 1 to 10 mass times, particularly preferably 1 to 5 mass times. When the amount is less than 0.1 mass times, purification efficiency decreases, so that the case is not preferred.

In the step of adding the hydrocarbon solvent to the compound of the formula [1] and stirring them, stirring for sufficient homogenization is preferably performed for 5 minutes or more.

"Step (B): a step of adding a buffer of pH 6 to 10 in an amount 0.5 mass time or more to the solution containing the compound of the formula [1] dissolved in the hydrocarbon solvent in the step (A) to extract the compound of the formula [1]"

The step (B) is a step of recovering the formula [1] dissolved in the step (A) from the hydrocarbon solvent and removing low polar impurities, mainly an antioxidant such as BHT contained in the formula [1].

The buffer is used for recovering the formula [1] from the above solvent. The pH of the buffer is 6 to 10, more preferably 7 to 9, particularly 7.5 to 8.5.

With regard to the pH of the buffer, when the pH is less than 6, decomposition of the acetal by an acid is induced, a polyacetal is formed, and an alcohol is produced as a by-product, so that the pH is preferably 6 or more. Moreover, with a strong base, since the base component reacts with chloroform or dichloromethane to be used in the next step, it is preferred to control the pH to 10 or lower. Usually used buffers, for example, a Tris buffer, a hydrochloride buffer, a phosphate buffer, a carbonate buffer, an imidazole buffer, a diethanolamine buffer, a triethanolamine buffer, Good's buffers such as HEPES and BICINE, and the like can be employed.

The amount of the buffer is preferably 0.5 mass time or more and more preferable range is 0.5 to 20 mass times. When the amount is less than 0.5 mass time, a recovery ratio from the solvent decreases owing to the small amount.

In the extraction operation in the step (B), the hydrocarbon solvent containing the formula [1] dissolved therein and the buffer are stirred and then allowed to stand. In order to extract the formula [1] from the organic layer sufficiently, they are stirred for 5 minutes or more and, after stirring is stopped, are allowed to stand for 5 minutes or more and then the aqueous layer is recovered after layer separation. An upper limit of the stirring time is not restricted but there is a concern that the acetal group may be hydrolyzed by long-time contact thereof with water, so that the time is preferably less than 5 hours. For the same reason, it is preferred to shorten the standing time as far as possible.

The temperature at the extraction with the buffer is desirably 5 to 40° C. When the temperature is lower than 5° C., there is a concern that precipitation of salts of the buffer may take place. Moreover, at a temperature higher than 40° C., there is a concern that the formula [1] may be decomposed owing to thermal history. The extraction operation may be performed repeatedly plural times in order to increase the recovery ratio.

"Step (C): a step of adding at least one extracting solvent selected from the group consisting of chloroform and dichloromethane in an amount 0.5 mass time or more to the buffer into which the compound of the formula [1] has been extracted in the step (B) to extract the formula [1]"

The step (C) is a step of extracting the compound of the formula [1] from the aqueous layer containing the formula [1] and water-soluble impurities, mainly a polyacetal compound dissolved therein, using chloroform or dichloromethane or a mixture thereof.

The amount of chloroform or dichloromethane to be used for extraction is 0.5 mass time or more, preferably 0.5 to 20 mass times, more preferably 1 to 20 mass times the amount of the compound of the formula [1]. When the amount is less than 0.5 mass time, the recovery of the compound of the formula [1] from the aqueous layer is poor and the yield becomes worse.

In the extraction operation in the step (C), the buffer containing the compound of the formula [1] dissolved therein and at least one solvent selected from the group consisting of chloroform and dichloromethane are stirred and allowed to stand. In order to extract the formula [1] from the aqueous layer sufficiently, they are stirred for 5 minutes or more and, after stirring is stopped, are allowed to stand for 5 minutes or more and then chloroform or dichloromethane is recovered after layer separation. An upper limit of the stirring time is not restricted but there is a concern of decomposition and polyacetalization with an acid contained in a minute amount by long-time contact with chloroform or dichloromethane, so that the time is preferably less than 5 hours. For the same reason, it is preferred to shorten the standing time as far as possible.

The temperature at the extraction is desirably 5 to 40° C. When it is lower than 5° C., there is a concern that precipitation of salts in the buffer may take place. Moreover, when it exceeds 40° C., odor resulting from vaporization of chloroform or dichloromethane is generated, so that the case is not preferred from the viewpoint of safety. Moreover, chloroform or dichloromethane is decomposed to generate hydrogen chloride and thus there is a concern that the acetal group may be decomposed.

"Step (D): a step of distilling the extraction solution obtained by extracting the compound of the formula [1] in the step (C), at 65° C. or lower under reduced pressure of 0.3 kPa or lower"

The step of (D) is a step of performing distillation for removing the alcohol and the polyacetal slightly contained in the formula [1]. It is a step of obtaining a highly pure formula [1] by performing distillation under reduced pressure at low temperature in order to suppress thermal deterioration of the acetal group.

When chloroform or dichloromethane remains in the extraction solution, decomposition of the acetal compound of the formula [1] is induced by an acid such as hydrogen chloride formed though decomposition of these solvents. This phenomenon is very disadvantageous for storing the compound of the formula [1]. Moreover, from a raw material which is the compound of the formula [1], upon the manufacturing the polyalkylene glycol derivative through addition polymerization of an alkylene oxide, since an alkali catalyst is used, the presence of chloroform or dichloromethane that reacts with a strong base becomes a problem.

Before distillation, it is preferred to remove low-boiling impurities such as the solvents used in the previous steps and the impurity alcohol by concentration. The temperature at the concentration is preferably 65° C. or lower. When the temperature is higher than 65° C., there is a concern that the acetal group of the formula [1] may be decomposed to form ethanol and the polyacetal as by-products. From this viewpoint, the temperature at the concentration is further preferably 60° C. or lower. Moreover, by controlling the temperature at the concentration to 20° C. or higher, time required for removal of the solvent can be shortened. From this viewpoint, the temperature at the concentration is further preferably 30° C. or higher.

Before distillation, for the purpose of removing water entrained at the extraction from the aqueous layer, an operation for dehydration may be performed. As methods for dehydration, azeotropic dehydration and a dehydration method with a desiccant may be mentioned. Since deterioration by thermal history becomes a problem in the azeotropic dehydration with a solvent having a boiling point close to that of water, it is preferred to perform dehydration using a desiccant. As the desiccant, for example, zeolite such as molecular sieves may be mentioned. When an acidic substance such as magnesium sulfate or calcium chloride is used as the desiccant, there is a concern that the acetal may be decomposed to form the alcohol or the polyacetal as by-products. The amount of the desiccant to be used is preferably 1 to 50% by mass of the formula [1]. The drying temperature is preferably 5 to 40° C.

By performing the distillation step at 65° C. or lower under reduced pressure of 0.3 kPa or lower, the acetal compound represented by the formula [1] can be obtained in good purity and in high yields. At the distillation, an inert gas may be introduced therein. In the case where a degree of vacuum is larger than 0.3 kPa, distillation temperature of the acetal compound is heightened and there is a concern that the acetal group may be decomposed. From this viewpoint, the degree of vacuum is further preferably 0.2 kPa or lower. Moreover, in the case where the distillation temperature is higher than 65° C., there arises a problem that the acetal group in the acetal compound may be decomposed also during the distillation to form the alcohol and the polyacetal as by-products and thus the yield becomes worse. From this viewpoint, the distillation temperature is further preferably 60° C. or lower. Furthermore, by controlling the distillation temperature to 20° C. or higher, time required for the distillation can be shortened. From this viewpoint, the distillation temperature is further preferably controlled to 30° C. or higher.

By performing the steps (A) to (D) sequentially, the highly pure formula [1] can be obtained. When this order is changed, it becomes impossible to remove the impurities.

BHT is a subliming substance and, in the case where BHT has not been removed before the distillation step (D), there is a concern that BHT may be included in a fraction of the formula [1], which is an objective compound, at the distillation. Even when the steps (A), (B), and (C) are performed thereafter, there is a possibility that the polyacetalization and the formation of the alcohol as a by-product may take place slightly and also, in order to remove the solvent used for extraction sufficiently, distillation should be again performed. For the above reasons, the order of the steps is of importance.

By the manufacture by the above method, there can be obtained a highly pure compound of the formula [1], which does not contain the reactive impurities such as the polyacetal, the alcohol, and the antioxidant. Moreover, by using the compound as a raw material, a highly pure polyalkylene glycol derivative having an aldehyde group can be manufactured. Namely, the compound of the formula [1] manufactured by the invention is useful as a raw material for drug delivery materials.

EXAMPLES

The following will further specifically describe the invention based on Examples.

The acetal compound having a hydroxyl group was analyzed by gas chromatography (GC). Using HP6890Plus manufactured by Agilent Company as a GC system, measurement was performed under the following conditions.

Detector: hydrogen flame ionization detector
Capillary column: HP-5 Cross-Linked 5% PH ME Siloxane
  30 m×0.32 mm×0.25 μm
Column temperature: 70° C., 4 minutes→temperature elevation to 240° C. at 5° C./min→240° C., 12 minutes
Injection temperature: 280° C.
Detector temperature: 250° C.
Carrier gas: helium
Flow rate: 23 cm/sec
Injection amount: 0.2 μl
Split ratio: 1:100

Evaluation of the polyethylene glycol derivative was performed by liquid chromatography. Using ALLIANCE manufactured by WATERS Company as a system of liquid chromatography, GPC and HPLC analyses were performed. Conditions for each analysis are shown below.

GPC Analysis
  Detector: RI
  Developing solvent: 100 mM sodium acetate, 0.02% $NaN_3$ buffer (pH 5.2)
  Flow rate: 0.5 ml/min
  Column: Ultrahydrogel 500+Ultrahydrogel 250 (WATERS)
  Column temperature: 30° C.
  Amount of sample: 5 mg/ml 20 μl
HPLC Analysis
Preparation of HPLC Sample
  After 2 ml of a 0.1M acetate buffer of pH 4.0 was added to 20 mg of a polyethylene glycol derivative and the whole was stirred, 68 μl of a 40 mg/ml methanol solution of p-aminobenzoic acid was added thereto, followed by stirring. Then, 128 µl of a 10 mg/ml aqueous solution of sodium cyanoborohydride was added and reacted at 75° C. for 2 hours under stirring.

Detector: RI
Developing solvent: 1.5 mM ammonium formate buffer (pH 8.0)
Flow rate: 1.0 ml/min
Column: ES-502N (Asahi Kasei Corporation)
Column temperature: 30° C.
Sample amount: 5 mg/ml 20 µl Detection of a polyethylene glycol derivative having a structure where ethylene oxide had been addition-polymerized to BHT was performed using $^1$H-NMR. JNM-ECP400 (JEOL NMR) was used as an NMR apparatus, DELTA was used as a control analysis system, and ALICE was used as a data analysis system. The following shows analytical conditions.

Solvent: deuterated chloroform (0.05% TMS)
Sample concentration: 25 mg/ml
Measurement temperature: 25° C.
Number of integration: 128

Example 1-1

In the following, tetrahydrofuran (THF) to be used was dehydrated on molecular sieves of 4 angstrom overnight. Inside of a 5 L four-neck flask was substituted with nitrogen gas and 2.2 kg of THF was placed therein, followed by cooling to 10° C. or lower. Then, 50 g of lithium aluminum hydride was placed therein and 250 g of ethyl 3,3-diethoxypropionate was added dropwise so that inner temperature did not exceed 10° C. After completion of the dropwise addition, temperature was elevated to 20° C. and reaction was carried out for 1 hour. After the reaction, 420 g of distilled water was added and the whole was stirred for 2 hours, then filtration was performed through No. 2 filtration paper, and subsequently a cake was washed with 1.1 kg of THF. The filtrate was concentrated at 40° C. to obtain 213 g of crude 3,3-diethoxy-1-propanol (hereinafter 33DEP).

Then, 200 g of crude 33DEP was placed in a 5 L four-neck flask and 1 kg of hexane was added thereto, followed by stirring for 1 hour (step (A)). After 1 kg of a 0.1M phosphate buffer (pH 7.5) was added and the whole was stirred for 20 minutes, it was transferred to a 5 L separatory funnel and allowed to stand until it was separated into layers. After an aqueous layer was taken out, a hexane layer was returned to the 5 L four-neck flask and 1 kg of the 0.1M phosphate buffer (pH 7.5) was again added. After stirring for 20 minutes, the whole was again transferred to the 5 L separatory funnel and allowed to stand until it was separated into layers and then an aqueous layer was recovered. The aqueous layer was recovered into the 5 L four-neck flask (step (B)). Then, 2 kg of chloroform was added thereto and, after stirring for 30 minutes, the whole was transferred to the 5 L separatory funnel and allowed to stand for 15 minutes to separate it into layers. A chloroform layer was recovered and an aqueous layer was returned to the 5 L four-neck flask and the same operations were performed with 2 kg of chloroform to recover a chloroform layer (step (C)). Then, the recovered chloroform layer was concentrated at 40° C. using an evaporator and, after evaporation ceased, the solvent was evaporated by bubbling with a minute amount of nitrogen. Thereafter, the product was stirred with 20 g of molecular sieves of 4 angstrom for 5 hours and then filtration was performed to obtain 188 g of 33DEP.

Then, 150 g of 33DEP obtained by the above operations was placed in a 300 ml four-neck flask and distillation was started under reduced pressure. A first fraction begun to be distilled at a degree of vacuum of 0.4 kPa, a bath temperature of 38° C., an inner temperature of 36° C., and a column top temperature of 33° C. After the distillation ceased, the bath temperature was gradually elevated and a main fraction begun to be distilled at a degree of vacuum of 0.2 kPa, a bath temperature of 58° C., an inner temperature of 55° C., and a column top temperature of 54° C. Thereafter, distillation was performed so that the column top temperature did not exceed 60° C. to obtain 138 g of the main fraction (step (D)). GC analysis was performed for the obtained main fraction. Results are shown in Table 1.

Example 1-2

Crude 33DEP was obtained by the method shown in Example 1-1. Then, 300 g of the crude 33DEP was placed in a 5 L four-neck flask and 1.5 kg of hexane was added thereto, followed by stirring for 1 hour (step (A)). After 1.5 kg of a 0.1M phosphate buffer (pH 7.5) was added and the whole was stirred for 20 minutes, it was transferred to a 5 L separatory funnel and allowed to stand until it was separated into layers. After an aqueous layer was recovered, a hexane layer was returned to the 5 L four-neck flask and 1.5 kg of the 0.1M phosphate buffer (pH 7.5) was again added. The same operations were performed and an aqueous layer was recovered (step (B)). Then, 3 kg of dichloromethane was added thereto and, after stirring for 30 minutes, the whole was transferred to the 5 L separatory funnel and allowed to stand for 15 minutes to separate it into layers. After a dichloromethane layer was recovered, an aqueous layer was returned to the 5 L four-neck flask and the same operations were performed with 3 kg of dichloromethane to recover a dichloromethane layer (step (C)). After the recovered dichloromethane layer was concentrated at 40° C., the solvent was further evaporated by bubbling with a minute amount of nitrogen. Thereafter, the product was stirred with 30 g of molecular sieves of 4 angstrom for 5 hours and then filtration was performed to obtain 277 g of 33DEP.

Then, 267 g of 33DEP obtained by the above operations was placed in a 500 ml four-neck flask and distillation was started. A first fraction begun to be distilled at a degree of vacuum of 0.4 kPa, a bath temperature of 35° C., an inner temperature of 33° C., and a column top temperature of 30° C. After the distillation ceased, the bath temperature was gradually elevated and a main fraction begun to be distilled at a degree of vacuum of 0.2 kPa, a bath temperature of 58° C., an inner temperature of 56° C., and a column top temperature of 55° C. Thereafter, distillation was performed so that the column top temperature did not exceed 60° C. to obtain 244 g of the main fraction (step (D)). GC analysis was performed for obtained 33DEP. Results are shown in Table 1.

Comparative Example 1-1

Crude 33DEP was obtained by the method shown in Example 1-1. After concentration at 40° C., 103 g of 33DEP was placed in a 300 mL four-neck flask and distillation was performed. A first fraction begun to be recovered at a degree of vacuum of 0.4 kPa, a bath temperature of 38° C., an inner temperature of 35° C., and a column top temperature of 29° C. After the distillation ceased, the bath temperature was gradually elevated. Then, a main fraction begun to be distilled at a degree of vacuum of 0.2 kPa, a bath temperature of 59° C., an inner temperature of 56° C., and a column top temperature of 54° C. Thereafter, distillation was performed so that the column top temperature did not exceed 60° C. to obtain 91 g of the main fraction. Namely, 33DEP was manufactured without performing the extraction step in the method of Example 1-1. GC analysis was performed for the obtained 33DEP. Results are shown in Table 1.

Comparative Example 1-2

Crude 33DEP was obtained by the method shown in Example 1-1 and the same extraction step as in Example 1-1 was performed. Then, 110 g of obtained 33DEP was placed in a 300 mL four-neck flask and distillation was performed. A first fraction begun to be recovered at a degree of vacuum of 0.4 kPa, a bath temperature of 35° C., an inner temperature of 33° C., and a column top temperature of 29° C. Thereafter, the bath temperature was gradually elevated and a main fraction begun to be recovered at a degree of vacuum of 0.5 kPa, a bath temperature of 72° C., an inner temperature of 70° C., and a column top temperature of 70° C. The distillation operation was performed until the distillation ceased at a column top temperature of 70° C. to obtain 59 g of the main fraction. Namely, 33DEP was manufactured with performing the distillation step at a column top temperature of 70° C. in the method of Example 1-1. After distillation, GC analysis was performed for the obtained main fraction. Results are shown in Table 1.

Comparative Example 1-3

GC analysis was performed using a sample before distillation in Example 1-1.

TABLE 1

| | Example | | Comparative Example | | |
|---|---|---|---|---|---|
| Item | 1-1 | 1-2 | 1-1 | 1-2 | 1-3 |
| 33DEP (%) | 99.84 | 99.91 | 99.19 | 98.14 | 99.16 |
| Polyacetal (%) | 0.003 | ND | ND | 1.262 | 0.041 |
| Ethanol (%) | 0.009 | 0.005 | 0.003 | 0.374 | 0.004 |
| BHT (%) | ND | ND | 0.247 | ND | ND |
| Chloroform (%) | 0.006 | 0.004* | 0.011 | 0.017 | 0.696 |
| Yield of main fraction (%) | 92.0 | 91.4 | 88.3 | 53.6 | — |

*dichloromethane content

Even when BHT was removed by the method of Example 1-1, the acetal compound could be obtained in high purity and in high yields by performing distillation at 65° C. or less. Moreover, as in Example 1-2, even when the extracting solvent to be used in the step (c) was changed to dichloromethane, the acetal compound could be obtained in high purity and in high yields.

In the case where the extraction step was not performed and distillation was performed without removing BHT as in Comparative Example 1-1, BHT was detected in the main fraction since BHT is a subliming substance. Thus, it was revealed that 33DEP was contaminated with BHT in the manufacturing method of Comparative Example 1-1.

As in Comparative Example 1-2, 33DEP manufactured via the extraction step was poor in stability and, when distilled at 70° C., a polyacetal and ethanol in the main fraction increased. This phenomenon becomes a cause of by-product formation of polyalkylene glycol derivatives having the polyacetal or ethanol as a terminal structure. Moreover, the distillation operation was continued until the distillation of the main fraction ceased at 70° C. but the yield was so bad as 53.6%. As a cause thereof, it is mentioned that 33DEP was decomposed by continuing distillation at 70° C. When distillation residue was subjected to GC analysis, the polyacetal compound was contained in such a large amount as about 80% and thus the decomposition of the acetal group was confirmed. Under the conditions of Comparative Example 1-2, it was revealed that the main fraction was contaminated with the polyacetal having a hydroxyl group, the contamination became a main cause of large decrease in yield of the main fraction, and the conditions are disadvantageous also in costs.

In the case where only the extraction step was performed but distillation was not performed as in Comparative Example 1-3, the presence of chloroform was observed. When chloroform remains, chloroform is decomposed to generate an acid such as hydrogen chloride and there is a concern of decomposition of the acetal group. Moreover, at the manufacture of the polyalkylene glycol derivative though addition polymerization of an alkylene oxide, an alkali catalyst is used and hence the presence of chloroform, which reacts with a strong base, becomes a problem.

Example 2

One litter of methanol was added to a 5 L autoclave and, after washing under reflux, methanol was discarded and the flask was dried at 120° C. for 5 hours under 0.8 kPa or lower.

In the 5 L autoclave, 10.0 g of a 28% methanol solution of sodium methylate and 210 g of dehydrated toluene were added to 59.2 g (0.40 mol) of 33DEP manufactured by the method shown in Example 1-1 and the whole amount of methanol was removed at 50° C. under 30 kPa or lower in an azeotropic manner with dehydrated toluene. After temperature was elevated to 120° C., 1.89 kg of ethylene oxide was added and polymerized. After 1.65 kg of the resulting polyalkylene glycol derivative was taken out, 0.95 kg of ethylene oxide was polymerized at 120° C. Thereafter, 0.49 g of 85% phosphoric acid was added to discontinue the reaction and 1.06 kg of a polyalkylene glycol derivative having an acetal group (HO-PEG-Acetal) was obtained.

To a 1 L four-neck flask were added 100 g of HO-PEG-Acetal, 400 g of toluene, and 0.1 g of BHT, and the whole was dehydrated under reflux with stirring. After cooling to 40° C., 1.1 g of triethylamine and 0.9 g of methanesulfonyl chloride were added and reaction was carried out at 40° C. for 3 hours. Then, 3.7 g of a 28% methanol solution of sodium methylate was added and reaction was carried out at 70° C. for 3 hours. After the reaction liquid was subjected to suction filtration using Nutsche on which a filter paper of 5 A had been placed, a filtration cake was washed with 100 g of toluene and 380 g of hexane was added to the resulting filtrate to effect crystallization. Suction filtration was again performed and 430 g of ethyl acetate was added to the resulting crystals. After the crystals were dissolved with heating at 40° C., cooling was performed to 30° C. and crystallization was effected by adding 330 g of hexane. After suction filtration, the crystals were dried to obtain 91 g of a compound (MeO-PEG-Acetal) where a terminal hydroxyl group of the polyalkylene glycol derivative having an acetal group was methoxylated.

To a 1 L beaker were added 90 g of MeO-PEG-Acetal and 1700 g of distilled water, and the whole was stirred at room temperature to effect dissolution. The pH was adjusted to 1.5 by adding 85% phosphoric acid to the aqueous solution and hydrolysis was performed for 2 hours. After the pH was adjusted to 6.5 with a 400 g/l aqueous solution of sodium hydroxide, 270 g of sodium chloride was added and dissolved and then a 400 g/l aqueous solution of sodium hydroxide was further added to adjust the pH to 7.0. After extraction with 900 g of chloroform, concentration was performed at 50° C. and then 270 g of ethyl acetate was added. After 4.5 g of magnesium sulfate was added and stirring was performed at 25° C. for 30 minutes, suction filtration was performed using Nutsche on which a filter paper of 5 A had been placed and hexane was added to the resulting filtrate to effect crystallization. Crystals were recovered by suction filtration and dried to obtain 79 g of a polyalkylene glycol derivative (MeO-PEG-CHO) having an aldehyde group. GPC, LC, and NMR analyses were performed for the resulting MeO-PEG-CHO.

Comparative Example 2-1

Using 33DEP obtained in Comparative Example 1-1, the same operations as in Example 2 were performed to obtain MeO-PEG-CHO. Namely, using 33DEP containing BHT as a raw material, GPC, LC, and NMR analyses were performed in the same manner as in Example 2. Analytical results are shown in Table 2.

Comparative Example 2-2

Using 33DEP obtained in Comparative Example 1-2, the same operations as in Example 2 were performed to obtain MeO-PEG-CHO. GPC, LC, and NMR analyses were performed in the same manner as in Example 2. Analytical results are shown in Table 2.

Comparative Example 2-3

Using 33DEP obtained in Comparative Example 1-3, the same operations as in Example 2 were performed.

TABLE 2

| | | Example | Comparative Example | | |
|---|---|---|---|---|---|
| | Analytical item | 2 | 2-1 | 2-2 | 2-3 |
| GPC | Number-average molecular weight (Mn) | 20590 | 20644 | 20262 | — |
| | Polydispersity (Mw/Mn) | 1.03 | 1.03 | 1.04 | — |
| HPLC | Aldehyde ratio (%) | 94.8 | 90.0 | 85.4 | — |
| NMR | BHT-PEG (%) | ND | 0.68 | ND | — |

As in Example 2, by using 33DEP manufactured by the invention as a raw material, it was possible to manufacture a highly pure polyalkylene glycol derivative having an aldehyde group, which had a molecular weight of 20,000, without forming BHT-PEG as a by-product.

As a result of Comparative Example 2-1, when ethylene oxide was polymerized to 33DEP without removing BHT beforehand, an impurity (BHT-PEG) where ethylene oxide was polymerized to the hydroxyl group of BHT was detected. There is a concern that this may invite heterogeneity of pharmaceuticals.

As a result of Comparative Example 2-2, when MeO-PEG-CHO was manufactured using 33DEP whose purity had been decreased by thermal deterioration, an aldehyde ratio was decreased. This is considered as follows: in thermally deteriorated 33DEP, decomposition of the acetal group was accelerated by heat at the ethylene oxide addition and thus the aldehyde ratio was decreased.

As for Comparative Example 2-3, upon the addition of sodium methylate, the solution became turbid owing to sodium chloride formed as a by-product. When the solution was analyzed on NMR, decomposition of the acetal was observed. When chloroform coexisted, since it reacted with an alkali catalyst, the alkali catalyst was consumed and thus MeO-PEG-CHO could not be synthesized.

While the invention has been described in detail and with reference to specific embodiments thereof, it will be apparent to one skilled in the art that various changes and modifications can be made therein without departing from the spirit and scope thereof.

The present application is based on Japanese Patent Application No. 2011-67148 filed on Mar. 25, 2011, and the contents are incorporated herein by reference. Also, all the references cited herein are incorporated as a whole.

What is claimed is:

1. A method for manufacturing an acetal compound represented by the following formula [1], the method comprising performing the following steps (A) to (D) sequentially:

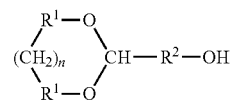

[1]

wherein n is 0 or 1 provided that $R^1$ groups may be bonded or may not be bonded to each other when n is 0; $R^1$ is an alkyl group having 1 or 2 carbon atoms or an alkylene group having 1 or 2 carbon atoms and the $R^1$ groups may be same or different from each other; and $R^2$ is an alkylene group having 1 to 6 carbon atoms, step (A): a step of dissolving the acetal compound represented by the formula [1] in a solvent made from a hydrocarbon having 5 to 8 carbon atoms in an amount 0.1 mass time or more the amount of the acetal compound to obtain a solution thereof, step (B): a step of adding a buffer of pH 6 to 10 in an amount 0.5 mass time or more the amount of the acetal compound to the solution obtained in the step (A) to extract the acetal compound into the buffer, step (C): a step of adding at least one extracting solvent selected from the group consisting of chloroform and dichloromethane in an amount 0.5 mass time or more the amount of the acetal compound to the buffer into which the acetal compound has been extracted, thereby extracting the acetal compound into the extracting solvent to obtain an extraction solution, and step (D): a step of distilling the extraction solution obtained in the step (C) at 65° C. or lower under a reduced pressure of 0.3 kPa or lower.

2. The method according to claim 1, wherein n is 0, $R^1$ is an ethyl group, and $R^2$ is an ethylene group or a 1-methylethylene group, in the acetal compound.

3. The method according to claim 1, wherein pH of the buffer in the step (B) is 7 to 9.

4. The method according to claim 2, wherein pH of the buffer in the step (B) is 7 to 9.

5. The method according to claim 1, wherein the amount of the hydrocarbon solvent in the step (A) is 0.1 to 10 mass times the amount of the acetal compound.

6. The method according to claim 2, wherein the amount of the hydrocarbon solvent in the step (A) is 0.1 to 10 mass times the amount of the acetal compound.

7. The method according to claim 3, wherein the amount of the hydrocarbon solvent in the step (A) is 0.1 to 10 mass times the amount of the acetal compound.

8. The method according to claim 4, wherein the amount of the hydrocarbon solvent in the step (A) is 0.1 to 10 mass times the amount of the acetal compound.

9. The method according to claim 1, wherein the amount of the buffer in the step (B) is 0.5 to 20 mass times the amount of the acetal compound.

10. The method according to claim 2, wherein the amount of the buffer in the step (B) is 0.5 to 20 mass times the amount of the acetal compound.

11. The method according to claim 3, wherein the amount of the buffer in the step (B) is 0.5 to 20 mass times the amount of the acetal compound.

12. The method according to claim 4, wherein the amount of the buffer in the step (B) is 0.5 to 20 mass times the amount of the acetal compound.

13. The method according to claim 1, wherein the amount of the extracting solvent in the step (C) is 0.5 to 20 mass times the amount of the acetal compound.

14. The method according to claim 2, wherein the amount of the extracting solvent in the step (C) is 0.5 to 20 mass times the amount of the acetal compound.

15. The method according to claim 3, wherein the amount of the extracting solvent in the step (C) is 0.5 to 20 mass times the amount of the acetal compound.

16. The method according to claim 4, wherein the amount of the extracting solvent in the step (C) is 0.5 to 20 mass times the amount of the acetal compound.

* * * * *